(12) United States Patent
Bodor et al.

(10) Patent No.: US 6,589,165 B2
(45) Date of Patent: Jul. 8, 2003

(54) MODULARLY STRUCTURED ENDOSCOPE

(75) Inventors: Zoltan Bodor, Cooper City, FL (US);
Matthias Zapletal, Leslieville (CA)

(73) Assignee: Surgical Optics Inc., Cooper City, FL (US)

( * ) Notice: Subject to any disclaimer, the term of this patent is extended or adjusted under 35 U.S.C. 154(b) by 3 days.

(21) Appl. No.: 09/802,950

(22) Filed: Mar. 12, 2001

(65) Prior Publication Data

US 2001/0023314 A1 Sep. 20, 2001

(30) Foreign Application Priority Data

Mar. 15, 2000 (DE) ......................................... 100 12 646
Oct. 11, 2000 (DE) ......................................... 100 50 247

(51) Int. Cl.[7] ................................................ A61B 1/06
(52) U.S. Cl. ........................ 600/172; 600/171; 600/162
(58) Field of Search ................................. 600/172, 112, 600/117, 125, 129, 132, 133, 136, 138, 142, 160, 161, 167, 176; 604/264

(56) References Cited

U.S. PATENT DOCUMENTS 5,876,330 A * 3/1999 Grabover et al. ........... 600/129
5,951,463 A * 9/1999 Lombardi et al. .......... 600/162

* cited by examiner

Primary Examiner—Teresa Walberg
Assistant Examiner—Vinod D. Patel

(57) ABSTRACT

The present invention is a modularly structured endoscope with an interchangeable image transmission unit and an endoscope casing which includes the optical fiber system. Due to the modular design, the light transmission unit can be repaired independently of the image transmission unit.

6 Claims, 3 Drawing Sheets

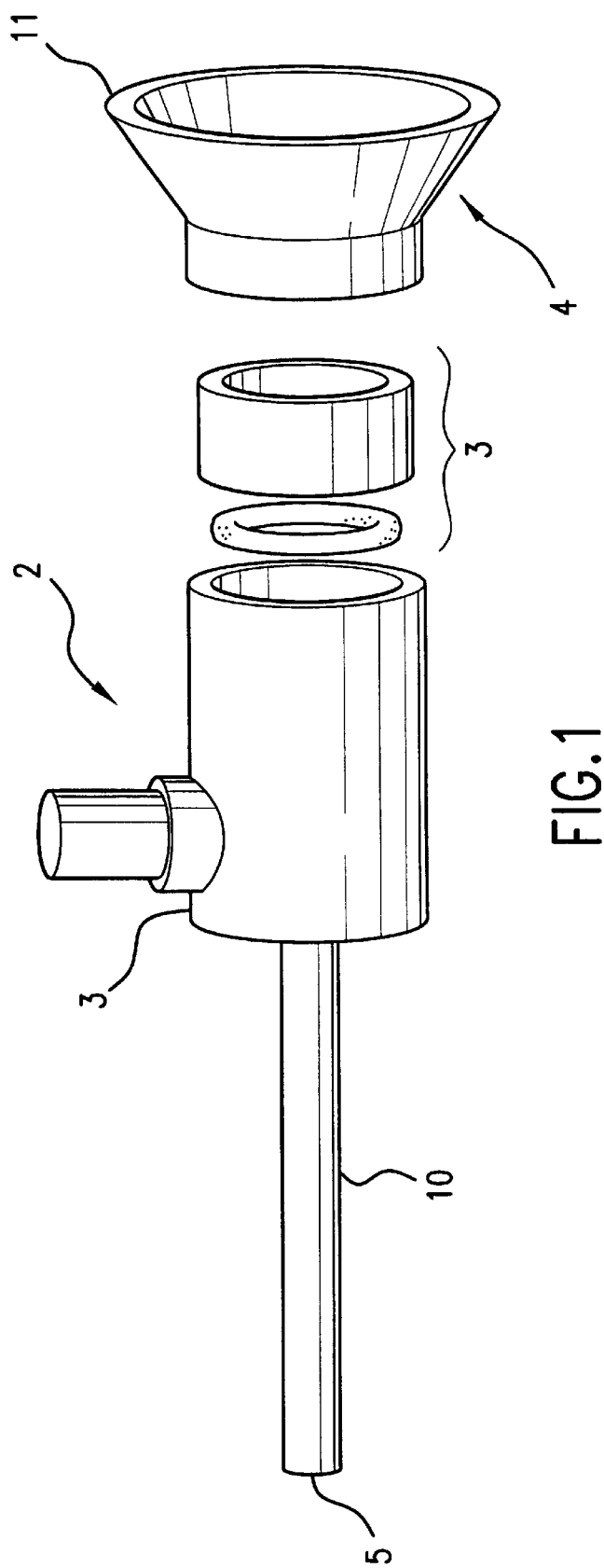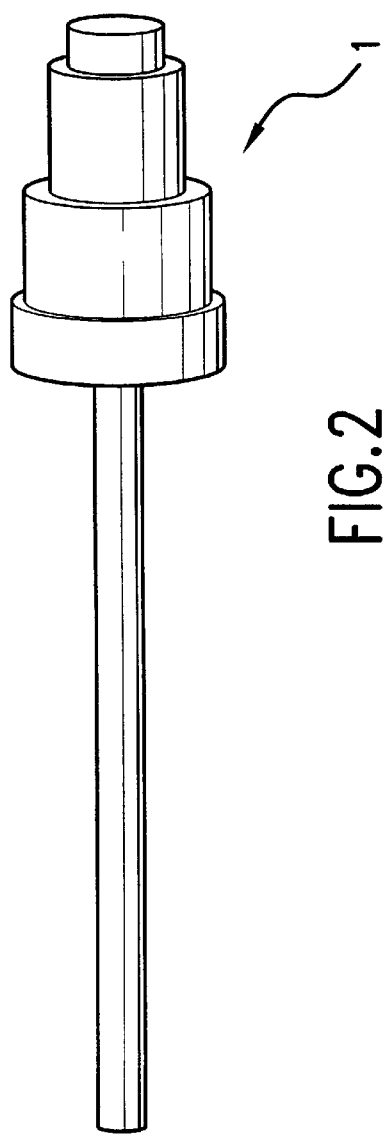

MODULARLY STRUCTURED ENDOSCOPE

BACKGROUND OF THE INVENTION

The present invention relates to a modularly structured endoscope with an interchangeable image transmission system, as well as processes for its production.

The use of highly sensitive optical instruments, like endoscopes, requires specific training for the handling of the instrument. If such an instrument is handled inexpertly or is mechanically overused, this may result in a partial or total failure of the optical components or of the entire system. In such a case, the whole instrument must be repaired properly.

It is an object of the present invention to overcome these difficulties, and provide easy-to-handle components, so even a non-expert can carry out the repair, thus enabling the quick reusability of the instrument within just a few minutes.

SUMMARY OF THE INVENTION

The present invention refers to a modularly structured endoscope containing a self-encapsulated image transmission system, which is fed with the necessary illumination for the image recording via an independent optical fiber system.

BRIEF DESCRIPTION OF THE DRAWINGS

FIG. 1 is an exploded perspective view of the optical fiber system of the modularly structure endoscope embodying the invention;

FIG. 2 is a perspective view of the optical image transmission system of the modularly structured endoscope embodying the invention;

DETAILED DESCRIPTION OF THE INVENTION

The present invention relates to endoscopes and to the handling, servicing and repair of an entire endoscope system, as well as its resistance to aggressive media like germicides and mechanical overuse.

The endoscope (see FIGS. 1 and 2) is made up of two main systems: the image transmission unit 1 and the endoscope casing including the optical fiber system 2, hereinafter called the light transmission unit 2. The endoscope has an interchangeable, closed image transmission unit 1 which can be opened and sealed through a sealing mechanism. Due to the modular design, the light transmission unit 2 can be repaired independently of the image transmission unit 1. If one of the units is damaged, the endoscope system will again be ready for operation within a few minutes by exchanging the damaged part.

According to the invention, this benefit is achieved because the image transmission unit 1 is entirely encapsulated and forms an independent modular unit. The encapsulation results from an interlocking, material-bonding, as well as non-positive connection. The independent light transmission unit 2 is completely sealed off at the distal end of the endoscope by a protective screen 5.

Figure 3:
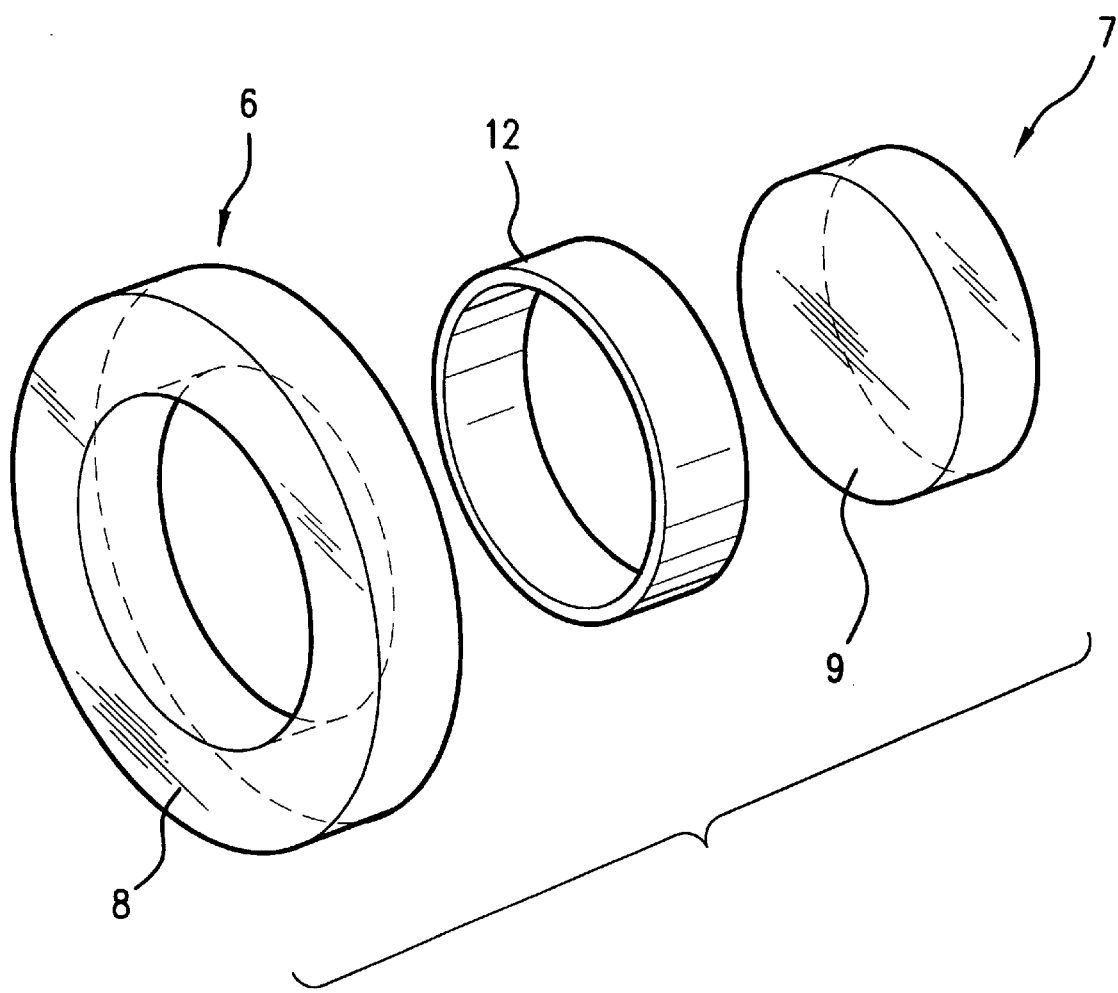
FIG. 3 is an exploded perspective view of the transparent part of the distal end of the endoscope tube with the light ring, viewing disk and metal ring.
Figure 4:
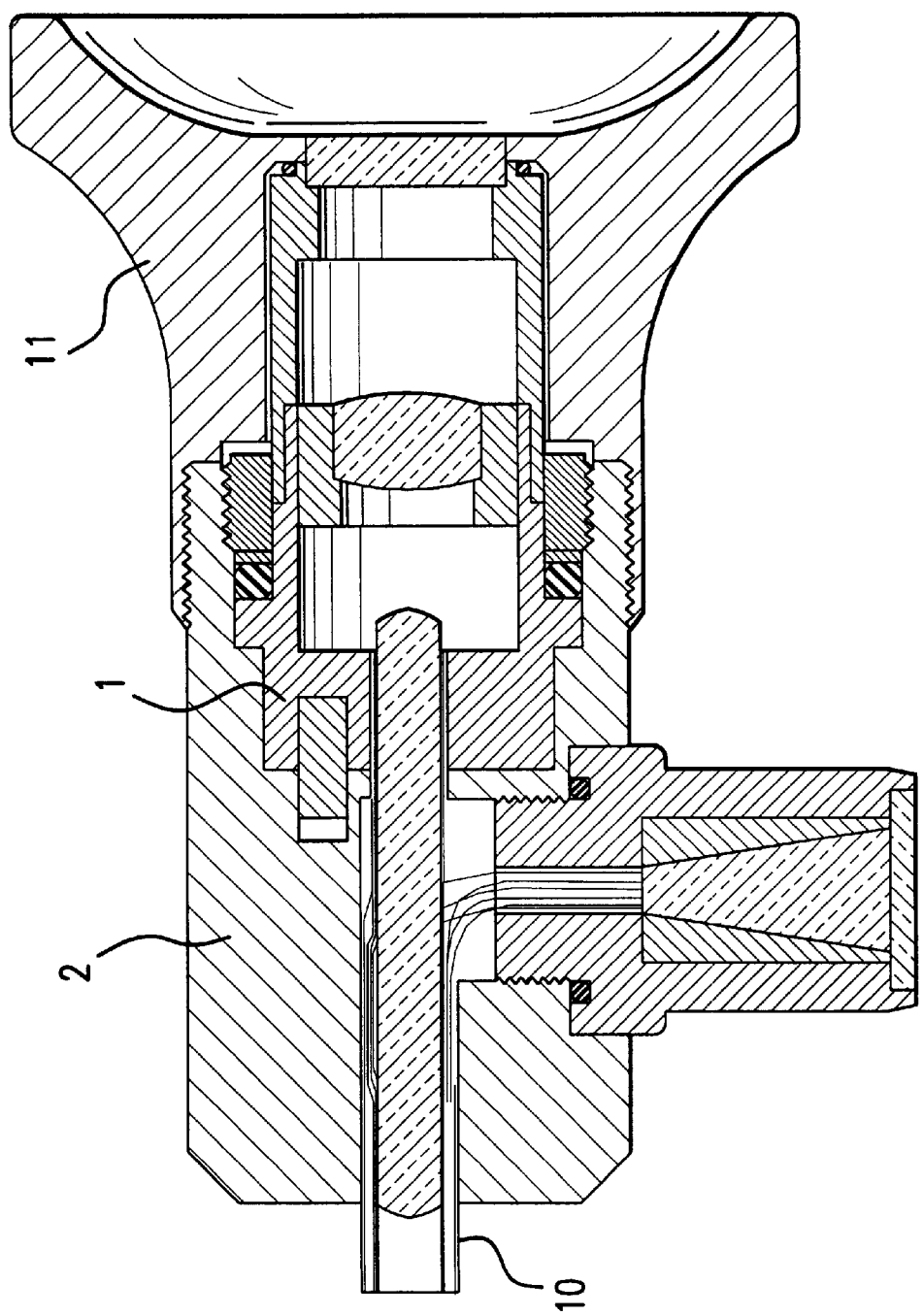
FIG. 4 is a cross sectional view of the optical image transmission system placed within the optical fiber system of the modularly structured endoscope.

The optical system for image transmission 1, as well as the optical fiber system 2 for illumination, are located inside of the endoscope and have no contact with body fluids and germicides. The ocular side 11 is sealed off by a material-bonding connection, as well as by a sealing unit. All material-bonding glued joints of the image transmission system 1 and the light transmission system 2 have no contact with their environment. In order to avoid scattered light from the optical fiber system during decoupling, the protective screen 5 at the distal end of the endoscope is constructed in two parts (see FIG. 3). The separation between the two protective screen parts 6 and 7, is achieved by means of a layer, or a tubular ring 12. The layer, or the tubular ring 12 are opaque to the visible range of light. In order to avoid reflections on the inside, between the optical system and the protective screen, the transmission of light and images can be improved through a fluid medium.

The transparent parts 6 and/or 7 can be made of glass, sapphire, or glass and sapphire. Further, the opaque means (ring and tubular layer 12) is preferably a metal material.

The endoscopic tube 10 is a metal material having the following desired characteristics: a tough hard consistency; shape memory; increased surface hardness and scratch resistance. These properties can be obtained by means of ion implantation.

The fixation or assembly system inside the endoscope is achieved through interlocking and is maintained by means of a mechanical latch.

The above-described endoscope can be utilized as a commercial endoscope for minimally invasive surgery and diagnostics or as a technical endoscope in industrial applications.

The present invention can further be adapted or modified by a person skilled in the art and the scope of the invention is only limited by the claims set forth below.

What is claimed is:

1. A modular endoscope, comprising:
   an image transmission unit having a housing,
   a tube extending from said image transmission housing,
   a light transmission unit for providing illumination,
   said light transmission unit having a housing,
   an endoscopic tube extending from said light transmission unit housing,
   wherein said image transmission unit is removably received within said light transmission unit.

2. The modular endoscope of claim 1, further comprising a protective screen at an end of said endoscopic tube.

3. The modular endoscope of claim 2, wherein said protective screen comprises a pair of transparent parts separated by a tubular layer.

4. The modular endoscope of claim 3, wherein said transparent parts are glass or sapphire.

5. The modular endoscope of claim 3, wherein said tubular layer is metal.

6. The modular endoscope of claim 1, further comprising optics within said image transmission unit housing.

* * * * *